United States Patent [19]

Tsukamoto et al.

[11] Patent Number: 5,434,120
[45] Date of Patent: Jul. 18, 1995

[54] USTILAGO TRICHOPHORA MYCOHERBICIDAL COMPOSITIONS AND METHODS OF USE

[75] Inventors: Hiroshi Tsukamoto; Hiroshi Tanaka; Naoto Nitta, all of Yokohama, Japan

[73] Assignee: Japan Tobacco Inc., Japan

[21] Appl. No.: 50,346

[22] PCT Filed: Sep. 17, 1992

[86] PCT No.: PCT/JP92/01184
§ 371 Date: Jun. 9, 1993
§ 102(e) Date: Jun. 9, 1993

[87] PCT Pub. No.: WO93/05656
PCT Pub. Date: Apr. 1, 1993

[30] Foreign Application Priority Data

Sep. 17, 1991 [JP] Japan .................. 3-310256

[51] Int. Cl.$^6$ .................................. A01N 63/04
[52] U.S. Cl. ............................. 504/117; 435/911
[58] Field of Search ............................... 504/117

[56] References Cited

U.S. PATENT DOCUMENTS

| | | | |
|---|---|---|---|
| 3,726,884 | 4/1973 | Aichenegg et al. | 504/182 |
| 3,849,104 | 11/1974 | Daniel et al. | 504/117 |
| 3,999,973 | 12/1976 | Templeton | 504/117 |
| 4,390,360 | 6/1983 | Walker | 504/117 |
| 4,419,120 | 12/1983 | Walker | 504/117 |

FOREIGN PATENT DOCUMENTS

| | | |
|---|---|---|
| 0374499 | 6/1990 | European Pat. Off. . |
| 2-13367 | 1/1990 | Japan . |
| 213367 | 1/1990 | Japan . |

OTHER PUBLICATIONS

Kalman Vanky, Symb. Bot. Upsal. XXIV:2, Carpathian Ustilaginales, pp. 246–247 (1985).
G. D. Gaikwad et al., J. Maharashtra Agric. Univ., Effects of Smut on Grain . . . , vol. 12, No. 2, pp. 246–247 (1987).
R. W. Barreto et al., Biological Abstracts, Taxonomy of a Fungus . . . , Abstract No. 77230, vol. 86, No. 8, (1988).
R. A. Fullerton, Biological Abstracts, New Plant Disease . . . , Abstract No. 11385, vol. 65, No. 2, (1977).
P. B. Chavan et al., J. Econ. Tax. Bot., A Preliminary Survey . . . , vol. 6, No. 1, pp. 239–244, (1985).
R. A. Fullerton et al., Biological Abstracts, A Study of Some Smuts . . . , Abstract No. 27881, vol. 51 (1970).

*Primary Examiner*—S. Mark Clardy
*Attorney, Agent, or Firm*—Birch, Stewart, Kolasch & Birch

[57] ABSTRACT

A herbicide useful for controlling weeds belonging to genus Echinochloa such as barnyardgrass, a method for controlling such weeds and novel microorganisms which can be used as an effective ingredient of the herbicide are disclosed. The present invention provides a herbicide comprising as an effective ingredient a microorganism belonging to genus Ustilago. The present invention also provides a method for controlling weeds by utilizing a microorganism belonging to genus Ustilago. The present invention also provides *Ustilago trichophora* B-171 (FERM BP-3968). The present invention further provides *Ustilago trichophora* B-174 (FERM BP-3969). The present invention further provides *Ustilago trichophora* B-185 (FERM BP-3970).

13 Claims, No Drawings

USTILAGO TRICHOPHORA MYCOHERBICIDAL COMPOSITIONS AND METHODS OF USE

This application is filed under 35 USC 37 from PCT/JP92/01184.

TECHNICAL FIELD

This invention relates to a herbicide, a method for controlling weeds and novel microorganisms belonging to genus Ustilago which can be used therefor.

PRIOR ART

Barnyardgrass (belonging to genus Echinochloa) which is an important weed in paddy and plowed fields is conventionally controlled mainly by chemical herbicides. In view of the environmental pollution caused by using agricultural chemicals in large amounts, it is desired to develop a herbicide and use thereof, which does not employ an agricultural chemical. A method for controlling weeds, which employs a pathogenic fungus which specifically attacks barnyardgrass, is known (Japanese Laid-open Patent Application (Kokai) No. 2-13367). However, the effectiveness of this method is not satisfactory, so that the herbicide and weeds-controlling method utilizing this pathogenic fungus are not widely used. Further, the conventional methods for controlling weeds utilizing chemical herbicides and the above-mentioned microorganism mainly aim at killing barnyardgrass.

DISCLOSURE OF THE INVENTION

An object of the present invention is to provide a novel microorganism which has an ability to control weeds such as barnyardgrass. Another object of the present invention is to provide a herbicide by which weeds such as barnyardgrass can be effectively and selectively controlled. Still another object of the present invention is to provide a method for effectively and selectively controlling weeds such as barnyardgrass.

The present inventors intensively studied to discover novel microorganisms pathogenic to barnyardgrass and that weeds such as barnyardgrass can be controlled by using the novel microorganisms, thereby completing the present invention.

The present invention provides a herbicide comprising as an effective ingredient a microorganism belonging to genus Ustilago. The present invention also provides a method for controlling weeds by utilizing a microorganism belonging to genus Ustilago. The present invention also provides *Ustilago trichophora* B-171 (FERM BP-3968). The present invention further provides *Ustilago trichophora* B-174 (FERM BP-3969). The present invention further provides *Ustilago trichophora* B-185 (FERM BP-3970). These microorganisms are deposited at the Fermentation Research Institute of Industrial Science and Technology, 1-3, Higashi 1-chome Tsukubashi Ibaraki-keen, 305, Japan (FERM BP-3970).

The microorganisms according to the present invention exhibit high virulences and selective pathogenicities to weeds such as barnyardgrass and do not adversely affect the growth of crops such as rice. Therefore, by using the microorganisms of the present invention, weeds can be effectively and selectively controlled. Further, unlike agricultural chemicals, the herbicide according to the present invention does not pollute or destroy environment.

BEST MODE FOR CARRYING OUT THE INVENTION

As mentioned above, the present invention provides *Ustilago trichophora* B-171 (FERM BP-3968), *Ustilago trichophora* B-174 (FERM BP-3969) and *Ustilago trichophora* B-185 (FERM BP-3970).

Synonyms of *Ustilago trichophora* include *Ustilago crus-galli* and *Ustilago sphaerogena*.

The novel microorganisms according to the present invention were first provided by collecting diseased barnyardgrass plants from various places in Japan, separating fungal strains pathogenic to barnyardgrass therefrom, pure culturing the separated strains, and by screening the pure cultured strains which are pathogenic to barnyardgrass but not pathogenic to other crops, particularly rice. The detailed method for first providing the microorganisms are described in the examples hereinbelow described.

The major mycological properties of the novel microorganisms are as follows:

They are aerobic. They grow well at a pH between 5 and 9. They grow at a temperature between 15°-35° C. and optimum growth temperature is 30°-35° C. The morphology and color in potato dextrose agar medium (hereinafter referred to as "PDA medium") are as follows:

The morphology of the colonies on PDA medium at the initial stage is white or pink, and smooth like colonies of yeasts. In the late stage, white mycelia grow from the surfaces of the colonies. Sexual spores are called teliospores or smut spores and are formed in the body of barnyardgrass plant which is the host. The sexual spores are black to dark brown and are spherical or oval with a diameter of about 9 $\mu$m. They have no septa and a number of spinelike protuberances are observed on the surfaces thereof. The teliospores germinate on the medium and form promycelium (basidium) having septa. On the promycelium, sporidia which are basidiospores are formed. The sporidia asexually grow by means of budding. The sporidia are hyaline, have cylindrical shape with a length of about 9 $\mu$m and a width of about 3 $\mu$m, and have no septa.

From these mycological properties, these microorganisms were identified as *Ustilago trichophora*. The strains B-171, B-174 and B-185 belonging to this species were deposited with FERMENTATION RESEARCH INSTITUTE OF JAPAN on Sep. 4, 1991, Feb. 5, 1992 and Feb. 5, 1992, respectively. All of these depositions were converted to international depositions under THE BUDAPEST TREATY on Aug. 18, 1992. The accession numbers of the international depositions are FERM BP-3968, FERM BP-3969 and FERM BP-3970, respectively. All of these strains have the above-described mycological properties. However, since their pathogenic powers are different as shown in the examples below, different strain names were given.

The novel microorganisms according to the present invention are pathogenic to the weeds belonging to genus Echinochloa such as barnyardgrass in paddy and plowed fields while not pathogenic to plants belonging to family Gramineae such as rice, wheat, barley, corn and Japanese barnyard millet; plants belonging to family Leguminosae such as soybean; plants belonging to family Solanaceae such as eggplant; and to plants belonging to family Cruciferae such as cabbage. As shown in the examples hereinbelow described, these microorganisms can be cultured in large scale and a large amount of spores can be obtained.

The herbicide according to the present invention is characterized by containing a microorganism belonging to genus Ustilago as an effective ingredient. Although the microorganism may be in the form of fungal mycelium, it is preferred that the microorganism be in the form of spores because spores have higher durability. The spores may be fresh spores immediately after cultivation or may be those restored from storage by using an aqueous medium. The storage can be carried out by the storage at a super low temperature ($-80°$ C.) or by lyophilization, which are well-known as the storing methods of microorganisms.

Although the herbicide according to the present invention may contain the above-described microorganism alone, it preferably contains one or more agricultural carriers widely used. Any agricultural carrier can be used as long as it does not adversely affect the microorganism, and water is best preferred. The population density of the spores suspended in water is not restricted but preferably not less than $10^6$ spores/ml, more preferably $10^7$–$10^9$ spores/ml. In suspending the spores in water, one or more adjuvants such as surfactants, and spreader and sticker may be added.

The herbicide according to the present invention may be applied at any growth stage of the weeds and before the germination of the weeds. Thus, the herbicide according to the present invention can be directly applied to the weeds or to the ground of paddy or plowed fields in which prevention of emergence of the weeds is desired. The amount of the herbicide to be applied can be appropriately selected depending on the growth stage, number and size of the weeds. When the herbicide is spread on the paddy or plowed field, the amount of the herbicide is preferably $10^9$ to $10^{11}$ in terms of the number of microorganisms per 1 m$^2$.

The novel microorganisms according to the present invention are pathogenic to the weeds belonging to genus Echinochloa such as barnyardgrass, which are weeds in paddy and plowed fields, and form gall or swelling in leaf sheaths so that the infected barnyardgrass plants are killed or their growth is extremely inhibited. Killing the weeds is not the only method for controlling the weeds in paddy fields. If the growth of the weeds is inhibited by the above-described microorganism, the growth of rice prevails the growth of the weeds, so that most of the sun light is received by the rice and the growth of the weeds in the shade of rice is further inhibited. As a result, it is thought that the damage by the weeds can be substantially reduced. Further, the barnyardgrass plants which are diseased and whose growth is inhibited cannot form ears, or even if they can form ears, they are sterile. When ears are infected with the microorganisms, the seeds are filled with the teliospores and are sterile, so that the emergence of the weeds in the next year is prevented. On the other hand, cultivated plants such as rice, wheat, Japanese barnyard millet, soybean, eggplant and cabbage are not infected with the microorganisms. Therefore, the target weeds can be selectively controlled.

(EXAMPLES)

1) Process for First Obtaining Novel Microorganisms of the Present Invention

Barnyardgrass plants grown on paddy and plowed field, which exhibited diseased symptoms were collected. The diseased portions were cut out and the mass of teliospores therein were taken out. The mass were immersed in 70% ethanol for 30 to 60 seconds and suspended in 0.5% sodium hypochlorite solution to which equivalent volume of 0.1% TWEEN 80 had been added, for 1–3 minutes to sterilize the surfaces thereof.

After washing the spores once with 0.1% TWEEN 80 solution and twice with sterilized water, they were streaked on an antibiotic-containing potato dextrose agar medium (hereinafter referred to as "APDA medium") and were germinated in an incubator at 25° C. Each of single colonies was transferred to a fresh PDA medium to carry out pure isolation of the microorganism and cultured in the incubator.

Each of the thus isolated strain was checked again for the pathogenicity to barnyardgrass, and its pathogenicities to rice, wheat, barley, corn, Japanese barnyard millet, soybean, eggplant and cabbage were examined. The strains B-171, B-174, B-185 according to the present invention which exhibit excellent herbicidal activities to barnyardgrass and which do not exhibit pathogenicities to rice, wheat, barley, corn, Japanese barnyard millet, soybean, eggplant and cabbage were isolated.

2) Identification of First Provided Microorganisms

The identification of the microorganisms according to the present invention was carried out by observing the morphologies of the teliospores and morphologies of germs on the medium. As a result, as described above, the microorganisms according to the present invention were identified as *Ustilago trichophora*.

3) Method for Culturing in Large Scale

To the microorganisms grown on PDA medium, sterilized water is added and stirred to prepare a suspension containing spores at a high concentration. About 100 $\mu$l of the suspension is dropped on a fresh medium and the drop is spread by using a sterilized L-shaped glass rod. By this method, inoculation of the microorganism to a large number of petri dishes (diameter: 9 cm) can be accomplished at one time and the time required for growing the microorganisms was largely reduced to 1–2 days. By this method, $5 \times 10^{10}$ spores per one petri dish were formed.

The microorganisms grown on PDA medium were inoculated to modified YPD liquid medium (containing 10 g of trypton, 5 g of yeast extract and 10 g of dextrose per one liter of water) by using a platinum loop and cultured under shaking for 2 days. As a result, $5 \times 10^8$ spores per 1 ml of culture medium were formed.

Thus, spores of the microorganisms according to the present invention can be easily obtained in a large amount by using the plate medium or liquid medium.

4) Test for Attacking Barnyardgrass (Virulence)

Barnyardgrass plants were grown in commercially available pots and the plants in 1–5 leaf stage were used as test materials.

The spores of the microorganisms according to the present invention, which were obtained by culturing the microorganisms on PDA medium or in modified YPD liquid medium were suspended in 0.1% TWEEN 80 solution and each of the suspensions was applied to barnyardgrass plants with an air spray. The inoculated plants were incubated at 22° C. for 24 hours in a moist chamber and then incubated for 5 weeks at 25° C. in a green house. Thereafter, the rates of diseased barnyardgrass plants were determined, which are shown in Table 1. By any of the strains, not less than 60% of the barnyardgrass plants were diseased. B-171 which exhibited the highest rate of diseased plants was checked for the relationship between the concentration of the inoculum and the rate of diseased plants. As shown in Table 2, it was proved that there is a correlation between the concentration and the rate of diseased plants. The heights of the barnyardgrass plants diseased by B-171 and those of healthy barnyardgrass plants were compared, which is shown in Table 3.

TABLE 1

| Strain and Rate of Diseased Plants | |
|---|---|
| Strain | Rate of Diseased Plants (%) |
| B-171 | 100 |
| B-174 | 70 |
| B-185 | 60 |

TABLE 2

| Concentration of Inoculum and Rate of Diseased Plants | |
|---|---|
| Concentration of Inoculum (spores/ml) | Rate of Diseased Plants (%) |
| 0 | 0 |
| $10^7$ | 69 |
| $10^8$ | 78 |
| $10^9$ | 100 |

TABLE 3

| Comparison of Heights of Diseased Barnyardgrass Plants and Healthy Barnyardgrass Plants | |
|---|---|
| | Height of Plant (cm) |
| Healthy Barnyardgrass | 90 |
| Diseased Barnyardgrass | 22 |

As is apparent from Tables 1, 2 and 3, the microorganisms according to the present invention exhibited excellent controlling effects against barnyardgrass.

5) Influence on Cultivated Plants

Pathogenicity tests against cultivated plants were carried out for B-171, B-174 and B-185 in the same manner as in the test of virulence against barnyardgrass. The concentration of the spores in the inoculum was $10^9$ spores/ml.

Rice, wheat, barley, corn, Japanese barnyard millet, soybean, eggplant and cabbage were used as the test plants. The results of the tests are shown in Table 4.

TABLE 4

| Pathogenicities Against Cultivated Plants | |
|---|---|
| Plant | Pathogenicity |
| Rice | − |
| Wheat | − |
| Barley | − |
| Corn | − |
| Japanese Barnyard Millet | − |
| Soybean | − |
| Eggplant | − |
| Cabbage | − |
| Barnyardgrass | + |

As is apparent from Table 4, the microorganisms according to the present invention did not exhibit pathogenicities to rice, wheat, barley, corn, Japanese barnyard millet, soybean, eggplant and cabbage.

What is claimed is:

1. A herbicide comprising a herbicidally effective amount of a microorganism selected from the group consisting of Ustilago trichophora B-171 (FERM BP-3968), Ustilago trichophora B-174 (FERM BP-3969) and Ustilago trichophora B-185 (FERM BP-3970) and an agricultural carrier therefor.

2. The herbicide according to claim 1, wherein the microorganism is in the form of fungal mycelium.

3. The herbicide according to claim 1, wherein the microorganism is in the form of spores.

4. The herbicide according to claim 1, wherein the agricultural carrier is water.

5. The herbicide according to claim 1, wherein the amount of the microorganism in the form of spores suspended in water is not less than $10^6$ spores/ml.

6. A herbicide comprising a herbicidally effective amount of a microorganism selected from the group consisting of Ustilago trichopora B-171 (FERM BP-3968), Ustilago trichophora B-174 (FERM BP-3969) and Ustilago trichophora B-185 (FERM BP-3970) and an agricultural carrier therefor, said herbicide being present in an amount effective against weeds belonging to genus Echinochloa.

7. A method for controlling weeds by applying a herbicidally effective amount of a microorganism selected from the group consisting of Ustilago trichopora B-171 (FERM BP-3968), Ustilago trichophora B-174 (FERM BP-3969) and Ustilago trichophora B-185 (FERM BP-3970) and an agricultural carrier therefor.

8. The method according to claim 7, wherein said weeds to be controlled are barnyardgrass.

9. The method for controlling weeds according to claim 7, wherein said microorganism is applied prior to the germination of weeds.

10. The method for controlling weeds according to claim 7, wherein the microorganism is applied to the weeds at any growth stage, or to the ground of the fields in which prevention of emergence of the weeds is desired.

11. The method for controlling weeds according to claim 7, wherein the microorganism is applied in the range of $10^9$ to $10^{11}$ microorganisms per 1 m$^2$.

12. A method for controlling weeds according to claim 7, wherein the microorganism is applied to cultivated plants selected from the group consisting of rice, wheat, Japanese barnyard millet, soybean, eggplant and cabbage.

13. A method for controlling weeds by applying a herbicidally effective amount of a microorganism selected from the group consisting of Ustilago trichopora B-171 (FERM BP-3968), Ustilago trichophora B-174 (FERM BP-3969) and Ustilago trichophora B-185 (FERM BP-3970), said weeds belonging to genus Echinochloa.

* * * * *